US010799132B2

(12) United States Patent
Negi et al.

(10) Patent No.: US 10,799,132 B2
(45) Date of Patent: Oct. 13, 2020

(54) MULTI-SITE ELECTRODE ARRAYS AND METHODS OF MAKING THE SAME

(71) Applicant: University of Utah Research Foundation, Salt Lake City, UT (US)

(72) Inventors: Sandeep Negi, Salt Lake City, UT (US); Rajmohan Bhandari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 424 days.

(21) Appl. No.: 15/271,062

(22) Filed: Sep. 20, 2016

(65) Prior Publication Data

US 2017/0007813 A1 Jan. 12, 2017

Related U.S. Application Data

(63) Continuation-in-part of application No. PCT/US2015/022045, filed on Mar. 23, 2015.

(Continued)

(51) Int. Cl.
*A61B 5/04* (2006.01)
*A61M 37/00* (2006.01)
(Continued)

(52) U.S. Cl.
CPC ........ *A61B 5/04001* (2013.01); *A61B 5/0478* (2013.01); *A61B 5/685* (2013.01); *A61B 5/6868* (2013.01); *A61M 37/0015* (2013.01); *A61N 1/0551* (2013.01); *A61B 5/14542* (2013.01); *A61B 2562/046* (2013.01);
(Continued)

(58) Field of Classification Search
CPC .................................................. A61B 5/04001
See application file for complete search history.

(56) References Cited

U.S. PATENT DOCUMENTS 5,215,088 A 6/1993 Normann et al.
7,006,859 B1 * 2/2006 Osorio ................. A61B 5/0478
600/378

(Continued)

FOREIGN PATENT DOCUMENTS

WO WO2013/173551 11/2013

OTHER PUBLICATIONS

PCT Application No. PCT/US2015/022045, Filing Date Mar. 23, 2015, Sandeep Negi International Search Report, dated Jun. 25, 2015, 11 Pages.

(Continued)

*Primary Examiner* — Lee S Cohen
(74) *Attorney, Agent, or Firm* — Thorpe North & Western, LLP

(57) ABSTRACT

A multi-site electrode array (100) can include a microneedle array and a set of electrically active sites (115). The microneedle array includes a plurality of microneedles (105) supported on a base substrate (110). The set of electrically active sites (115) can be arranged at and/or near the tip of each microneedle (105), and in many cases along a shaft of the microneedles. Further, at least a portion of the active sites (115) can be independently electrically addressable such that a remaining portion of the active sites (115) are optionally electrically shunted together. In some cases all of the active sites (115) are independently electrically addressable.

25 Claims, 11 Drawing Sheets

Related U.S. Application Data

(60) Provisional application No. 62/002,078, filed on May 22, 2014, provisional application No. 61/968,781, filed on Mar. 21, 2014.

(51) Int. Cl.
    *A61N 1/05*           (2006.01)
    *A61B 5/00*           (2006.01)
    *A61B 5/0478*        (2006.01)
    *A61B 5/145*         (2006.01)

(52) U.S. Cl.
    CPC ............... *A61M 2037/0053* (2013.01); *A61M 2037/0061* (2013.01); *A61M 2205/3303* (2013.01); *A61M 2205/3317* (2013.01); *A61M 2210/0693* (2013.01)

(56) References Cited

U.S. PATENT DOCUMENTS

| | | | |
|---|---|---|---|
| 8,255,061 B2* | 8/2012 | Perlin | A61B 5/04001 600/377 |
| 8,630,711 B1 | 1/2014 | Wark et al. | |
| 9,095,267 B2* | 8/2015 | Halpern | A61B 5/0478 |
| 2002/0106496 A1 | 8/2002 | Moxon et al. | |
| 2003/0100823 A1 | 5/2003 | Kipke et al. | |
| 2006/0085056 A1 | 4/2006 | Schouenborg | |
| 2006/0276866 A1 | 12/2006 | Mccreery | |
| 2007/0169333 A1 | 7/2007 | Donoghue et al. | |
| 2007/0197892 A1 | 8/2007 | Shen et al. | |
| 2009/0118806 A1 | 5/2009 | Vetter et al. | |
| 2009/0246515 A1 | 10/2009 | Negi et al. | |
| 2009/0301994 A1 | 12/2009 | Bhandari et al. | |
| 2010/0041972 A1 | 2/2010 | Mason | |
| 2010/0168830 A1 | 7/2010 | Hung et al. | |
| 2010/0178810 A2* | 7/2010 | Aarts | A61B 5/0478 439/676 |
| 2011/0106229 A1 | 5/2011 | Ortmann et al. | |
| 2012/0027946 A1 | 2/2012 | Steele et al. | |
| 2012/0138335 A1 | 6/2012 | Tathireddy et al. | |
| 2013/0131482 A1 | 5/2013 | Fedder et al. | |
| 2013/0144145 A1 | 6/2013 | Meng | |
| 2013/0167360 A1 | 7/2013 | Masmanidis et al. | |
| 2013/0237789 A1 | 9/2013 | Cattaneo | |

OTHER PUBLICATIONS

Wise et al, Wireless Implantable Microsystems: High-Density Electronic Interfaces To The Nervous System; Proceedings Of The IEEE; IEEE; Nov. 8, 2004; vol. 92 Issue 1; pp. 76-97.

McNaughton et al, The Stereotrode: A New Technique For Simultaneous Isolation Of Several Single Units In The Central Nervous System Form Multiple Unit Records; Journal Of Neuroscience Methods; Elsevier; Aug. 1983; vol. 8 Issue 4; pp. 391-397.

Harris et al, Accuracy Of Tetrode Spike Separation As Determined By Simultaneous Intracellular And Extracellular Measurements; Journal Of Neurophysiology; The American Physiological Society; Jul. 1, 2000; vol. 84 pp. 401-414.

Maynard et al, The Utah Intracortical Electrode Array: A Recording Structure For Potential Brain-Computer Interfaces; Electroencephalography And Clinical Neurophysiology; Elsevier; Mar. 1997; vol. 102 Issue 3; pp. 228-239.

Bhandari et al, Wafer-Scale Fabrication Of Penetrating Neural Microelectrode Arrays; Biomedical Microdevices; Springer; Oct. 2010; vol. 12 Issue 5; pp. 797-807.

Normann et al, Technology Insight: Future Neuroprosthetic Therapies For Disorders Of The Nervous System; Nature Clinical Practice Neurology; Nature Publishing Group; Sep. 2007; vol. 3 Issue 8; pp. 444-452.

Hoogerwerf et al, A Three-Dimensional Microelectrode Array For Chronic Neural Recording; Transactions On Biomedical Engineering; IEEE; Aug. 6, 2002; vol. 41 Issue 12; pp. 1136-1146.

Baker et al, Multi-Scale Recordings For Neuroprosthetic Control Of Finger Movements; Engineering In Medicine And Biology Society; IEEE; Sep. 2009; pp. 4573-4577.

Bragin et al, Multiple Site Silicon-Based Probes For Chronic Recordings In Freely Moving Rats: Implantation, Recording And Histological Verification; Journal Of Neuroscience Methods; Elsevier; May 15, 2000; vol. 98 Issue 1; pp. 77-82.

Shoham et al, Statistical Encoding Model For a Primary Motor Cortical Brain-Machine Interface; Transactions On Biomedical Engineering; IEEE; Jun. 13, 2005; vol. 52 Issue 7; pp. 1312-1322.

Bhandari et al, Wafer-Scale Processed, Low Impedance, Neural Arrays with Varying Length Microelectrodes; Solid-State Sensors, Actuators And Microsystems Conference; IEEE; Jun. 21-25, 2009.

Thomas Recording; Neuroscience Products; http://www.thomasrecording.com/neuroscience-products/metal-microelectrodes/tetrodes/; Accessed on Sep. 20, 2016.

* cited by examiner

MULTI-SITE ELECTRODE ARRAYS AND METHODS OF MAKING THE SAME

RELATED APPLICATIONS

This application is a continuation-in-part of PCT Application No. PCT/US15/22045, filed Mar. 23, 2015, which claims priority to U.S. Provisional Application No. 61/968,781, filed Mar. 21, 2014, and U.S. Provisional Application No. 62/002,078, filed May 22, 2014, which are incorporated herein by reference.

GOVERNMENT INTEREST

This invention was made with government support under NS085213 awarded by the National Institutes of Health. The government has certain rights in the invention.

BACKGROUND

The potential for implanting electronic devices into patients with direct interface to the neural system is vast. Systems which may enable paraplegics to regain control of their bladder or limbs, provide vision fix the blind, or restore vocal cord function are all under development, and promising initial results have been obtained in some experiments.

A key component of some implantable systems is a needle array to enable interfacing of the electronics with a nerve or directly with neurons in brain tissue. For example. U.S. Pat. No. 5,215,088 to Norman et al. discloses a three-dimensional electrode device which can be used as a neural or cortical implant. The device of Norman, also known as the Utah Electrode Array (UEA), can be used to provide a neural interface to electronic equipment for sensing and stimulation of physiological signals and pathways and has been successfully used in a large number of patients. However, difficulties and challenges of this system are still present which limit its effectiveness and potential applications. Although electrode arrays can include hundreds of needles in a small area, each of these needles can still potentially receive signals from thousands of neurons. Therefore, the ability of the electrode array to accurately record impulses from neurons is limited.

SUMMARY

A multi-site electrode array can include a microneedle array and a set of electrically active sites. The microneedle array includes a plurality of microneedles supported on a base substrate. The set of electrically active sites can be arranged at and/or near the tip of each microneedle, and in many cases along a shaft of the microneedles. Further, at least a portion of the active sites can be independently electrically addressable such that a remaining portion of the active sites are optionally electrically shunted together. In some cases all of the active sites on the microneedle are independently electrically addressable.

Fabrication of the multi-site electrode array can include forming the array of microneedles supported on a base substrate. The method can further include depositing electrically conductive traces along shafts of the microneedles to form a set of electrically active sites arranged on each microneedle. Within each set of active sites, at least a portion of the active sites can be independently electrically addressable from one another. The microneedles can also be insulated with an insulator such that at least one, and in some cases all, active sites of each set are exposed.

A multi-site channel array can include a microneedle array including a plurality of microneedles supported on the based substrate. The multi-site channel array can also include a set of channels arranged on each microneedle. Each channel in the set can be independent of one another and each can have an active site at a distal end of the channel.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
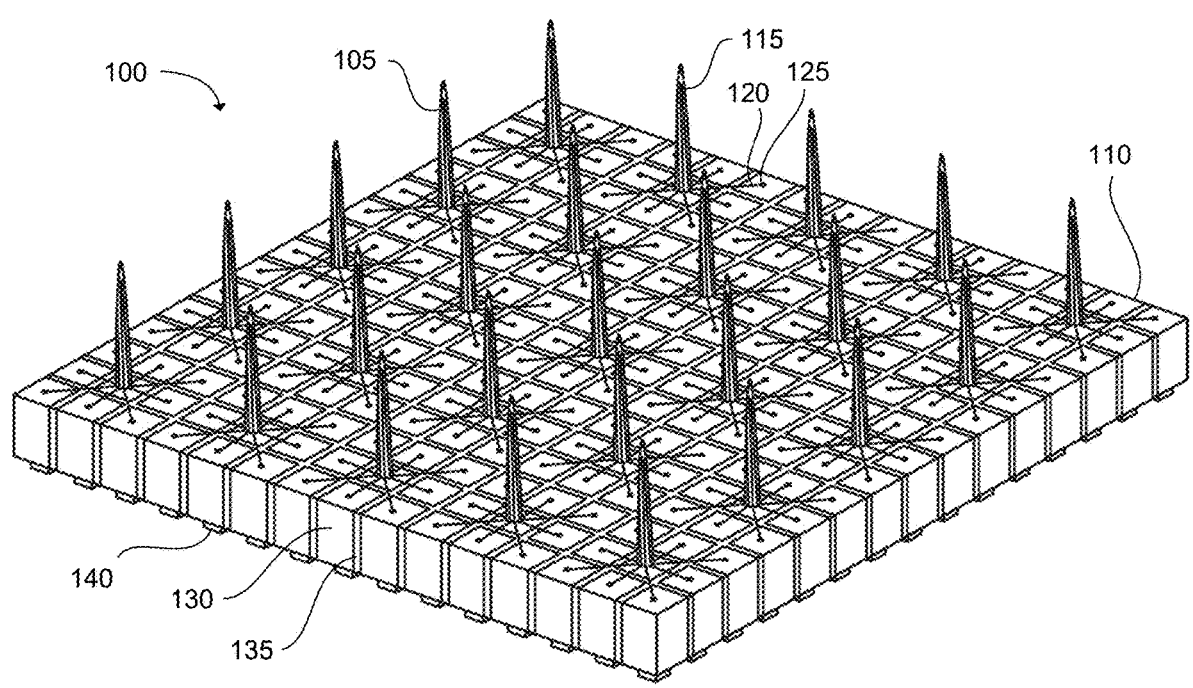
FIG. 1 is a perspective view of a multi-site electrode array in accordance with an embodiment of the present technology.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a layer" includes reference to one or more of such materials and reference to "depositing" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Multi-Site Electrode Arrays

Research into neutral network dynamics has progressed from recording neural signals using single electrodes, to multiple single electrode recordings, and more recently to arrays of recording electrodes. Although electrode arrays have allowed for access of up to a few hundred unique neuronal sources, the electrode arrays are still able to observe only a small fraction of the thousands of neurons within the recording radius of each electrode. Furthermore, signals recorded by the electrodes can be unreliable because of difficulty in distinguishing between signals from multiple neurons within the recording radius of the electrodes. Increasing the number of neurons that can be recorded from or increasing the reliability of each neuronal recording can improve upon the present understanding of the neural network.

Increasing the number of micro-needles in an electrode array can potentially increase the resolution of neuronal recordings. However, implantation of micro-needle electrode arrays necessarily causes insult to surrounding tissue when such an electrode array is implanted. Increasing the number of micro-needles can increase the insult to the tissue. Hence, design considerations for achieving the goal of increasing resolution of neural recordings include: placing a larger number of electrode sites in a small amount of tissue without significant tissue damage and efficient isolation of action potentials emanating from individual neurons.

In accordance with the present invention, one method of achieving this goal is to form electrode arrays having multiple electrically active sites on each micro-needle shaft. Including multiple active sites on each micro-needle can provide several advantages. For example, single-unit sorting can be improved by taking advantage of the temporal coherence of spikes from closely spaced recording sites. A 3D spatial location can also be identified by a set of recording sites that can define 3D volume. This approach also enables bi-polar stimulation and flexibility of selecting a channel close to the nucleus when targeting was not accurate. For recording electrodes, multiple sites also enable the simultaneous recording from a volume of tissue. For stimulation, a larger composite site increases the effective site area to allow increased charge injection while maintaining safe electrochemical and biological limits. This also allows, for example, precise current steering to selectively stimulate neural structures. For recording, a composite site can be used to change the recording selectivity of the device to emphasize, for example, field potential recording over single-unit recordings. Longevity of a recording electrode can also be improved by multiple sites. The lifetime of each site is different and follows some probability models. A subset of the sites can continue to function long after other ones have failed. Therefore, having more sites per electrode array can prolong the utility lifetime of the electrode array. Multiple sites can provide a spatial channel arrangement capable of more accurately representing activity within the adjacent volume for much longer periods of time than possible with single site microelectrodes.

In some cases, multiple active sites can be electrically connected to act as a single effective electrode. For example, a stereotrode is a pair of electrodes acting as a single effective electrode. A tetrode is a set of four electrodes acting as a single effective electrode. Tetrodes can improve the ability to reliably record extracellular neuronal events by providing multiple views of the same neuronal source. Further, tetrodes allow one to estimate the distance to the neuronal source or, given adequate data, the location of the source relative to the set of electrodes.

The tetrode technique relies on the fact that action potential amplitude is a declining function of distance between the electrode tip and the cell. Therefore, if cellular activity is recorded from four closely spaced electrode contacts the relative amplitudes of the spikes on the four channels can be used as an additional criterion for spike separation. Moreover, if the spikes from a given cell changes shape and/or amplitude, as occurs during burst firing, these changes are proportionally the same on the four channels, thus allowing accurate identification of these cells. Not only does the method reduce errors in classification, but it also increases the number of cells that can be identified.

In the past, stereotrodes and tetrodes have been fabricated by twisting multiple wires into a bundle. This process is not well suited for consistent results. Thomas Recording has developed a manufacturing process for single shaft tetrodes from quartz glass. However, because of technological limitation, this process has limited design options with respect to electrode placement, size, materials, and so on.

Multiple shank electrode devices, commonly called electrode arrays, are collections of multiple single electrodes in a rigid configuration. Several such electrode arrays have been developed in the past. Examples include the Utah Electrode Array (UEA), the Michigan Probe, and Microwire Arrays. Of these, the UEA and the Michigan Probe are manufactured using Micro-electrical Mechanical Systems (MEMS) technologies, providing both repeatable manufacturing and ability to make very fine structures. Table 1 compares several existing electrode technologies with the electrode arrays having multiple electrically active sties on each shaft as described herein (identified in the table as "Multisite Electrode Array").

TABLE 1

| Characteristics | Twisted Wire Tetrode | Michigan Probe | Thomas Recording | Multisite Electrode Array |
| --- | --- | --- | --- | --- |
| Electrode size | Macro | Micro | Macro | Micro |
| Reproducibility | Limited | Good | Limited | Good |
| Impedance | MOhm | kOhm | MOhm | MOhm |
| Customization | Limited | Yes | Limited | Yes |
| Precision | Not good | Good | Better | Good |
| Spatial resolution | Not good | One side | Better | Full 3D mapping |
| Active sites | Tip | One side of shaft | Tip and all sides of shaft | Tip and all sides of shaft |

In a general sense, the Michigan Probe and the UEA both have an array of electrodes distributed on a plane with the orientation of the plane differing between the two devices. The recording plane of the UEA is parallel to the surface of cerebral cortex, thereby placing multiple electrodes approximately in the same cortical lamina whereas the recording plane of the Michigan Probe is normal to the cortical surface, thereby placing electrodes in a line across the surface but in multiple lamina. Thus, the UEA samples a larger region across the cortical surface but with only one representation (lamina) whereas the Michigan Probe samples a greater range of representations (lamina) but across a smaller region. It is possible to create a three dimensional (3D) array of electrodes with the Michigan Probe but the active sites are only on one side of the array and hence cannot map 3D neuronal space. Furthermore, though it is possible to create tetrode configurations in the Michigan Probe, the device can sample at only one position across cortex.

The UEA is FDA approved and has been extensively used in human clinical trials as a brain-machine interface to provide useful function to the paralyzed. The UEA structure distributes its electrodes at regular spacing over a large region of the cortical surface, thereby providing a rich feature set of neuronal information. This structure also implies that the data from any given electrode may be the only source of such information and, therefore, the UEA is not always a robust source of information.

The multisite electrode arrays in accordance with the present technology can improve upon previous electrode technologies, by providing electrodes covering a wide area of the cortical surface as well as in multiple lamina. Thus, the multisite electrode arrays can provide information about neuronal activity within a 3D volume. The multiple active sites of the multisite electrode arrays can also provide more robust information about neuronal activity.

In accordance with the present technology, an implantable, multisite electrode array can include a microneedle array supporting multiple sets of electrically active sites on each microneedle. The microneedle array includes multiple microneedles supported on a base substrate. A set of electrically active sites can be arranged at and near the tip of each microneedle, and along a shaft of the microneedle. Further, at least a portion of the active sites, and in some cases all active sites, can be independently electrically addressable.

FIG. 1 shows an exemplary embodiment of the present technology. A multi-site electrode array 100 has a 5×5 array of microneedles 105 supported by a substrate 110. Each microneedle has a set of electrically active sites 115 that are independently addressable. In this embodiment, one electrically active site is at the tip of the microneedle, and eight additional electrically active sites are arranged on the shaft of the microneedle. The number of independently addressable active sites is not particularly limited, only by deposition resolution, microneedle surface area, and practical considerations. However, in current cases, the number of active sites can range from 4 to about 50, and in some cases from 6 to 15. The electrically active sites on the shaft are connected to electrically conductive lead lines 120 that lead down the shaft and branch out to base contacts 125. Each microneedle is at the center of a 3×3 grid of silicon wells 130 separated by insulating glass kerfs 135. The lead lines and base contacts allow electrical signals to be transmitted from the electrically active sites on the shaft to the silicon wells. Bond pads 140 are oriented on the underside of each silicon well. The bond pads allow for connection of a controller and current source to each independently addressable electrically active site.

Figure 2:
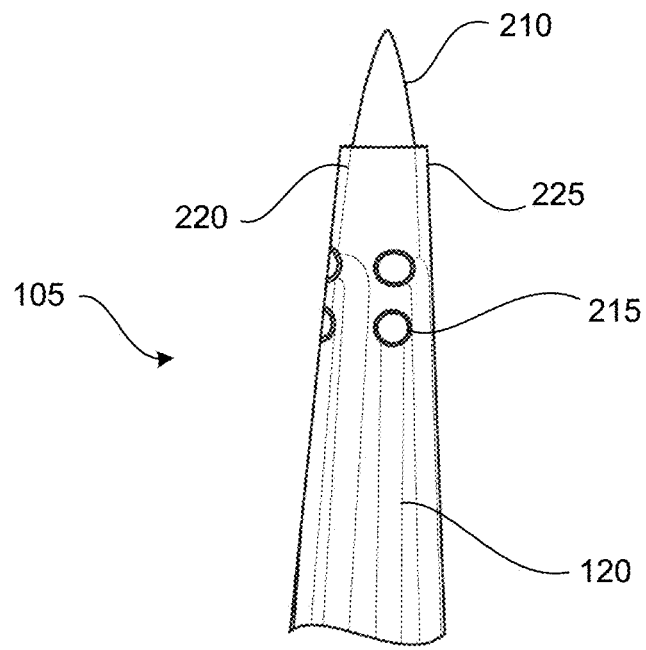
FIG. 2 is a close up view of a tip of a microneedle in accordance with an embodiment of the present technology.

FIG. 2 shows a side view of a microneedle 105 in accordance with an embodiment of the present technology. This microneedle includes an electrically active tip 210 and a set of circular electrically active sites 215 arranged on the shaft of the microneedle. Each electrically active site is connected to a lead line 120 running down the shaft. This allows the electrically active sites to be independently addressable. The tip is addressable through an electrically conductive core 220 of the microneedle. The tip and the core of the microneedle can be formed of a single, continuous electrically conductive material. An electrically insulating coating 225 covers the microneedle. However, the tip and the electrically active sites on the shaft are exposed, e.g., not covered by the insulating coating.

A layer of insulating coating can be oriented between each of the lead lines and the electrically conductive core. Therefore, each electrically active site can be isolated so that each is independently addressable.

Figure 3:
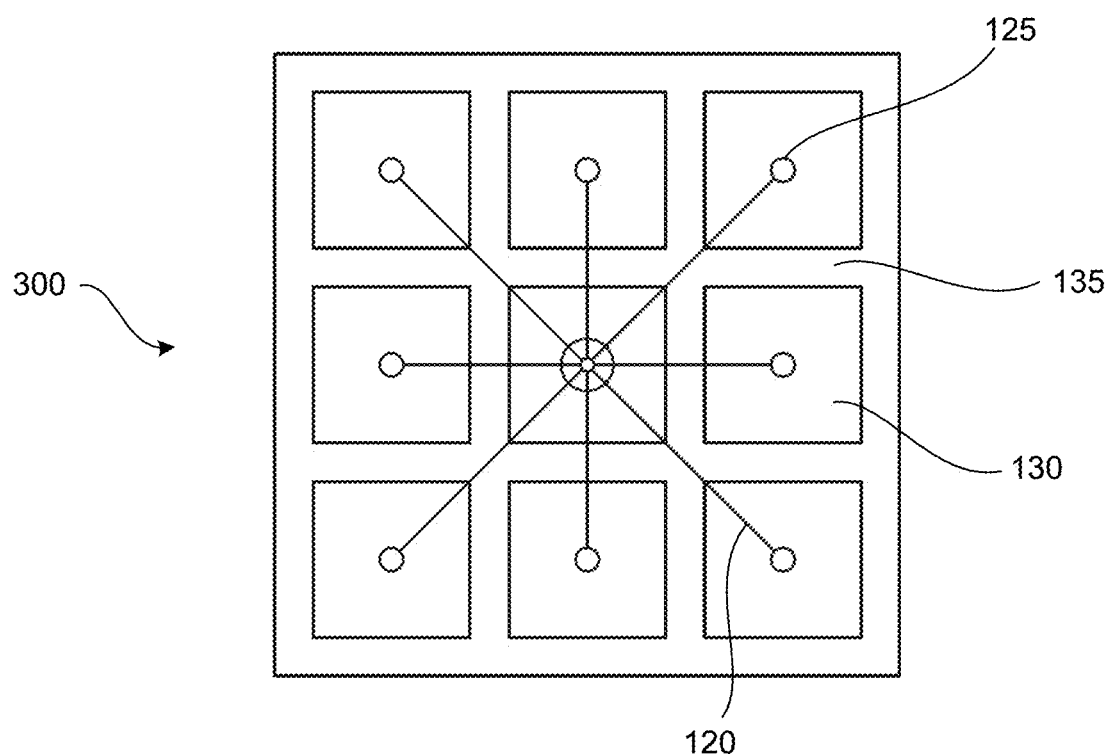
FIG. 3 is a top-down view of a 3×3 grid substrate which can be placed under a single microneedle, in accordance with an embodiment of the present technology.

FIG. 3 shows a top-down view of a 3×3 grid unit 300 of the substrate. Lead lines 120 run from the microneedle to base contacts 125. The base contacts provide an electrical connection to silicon wells 130. The silicon wells are separated by electrically insulating glass kerfs 135.

Figure 4:
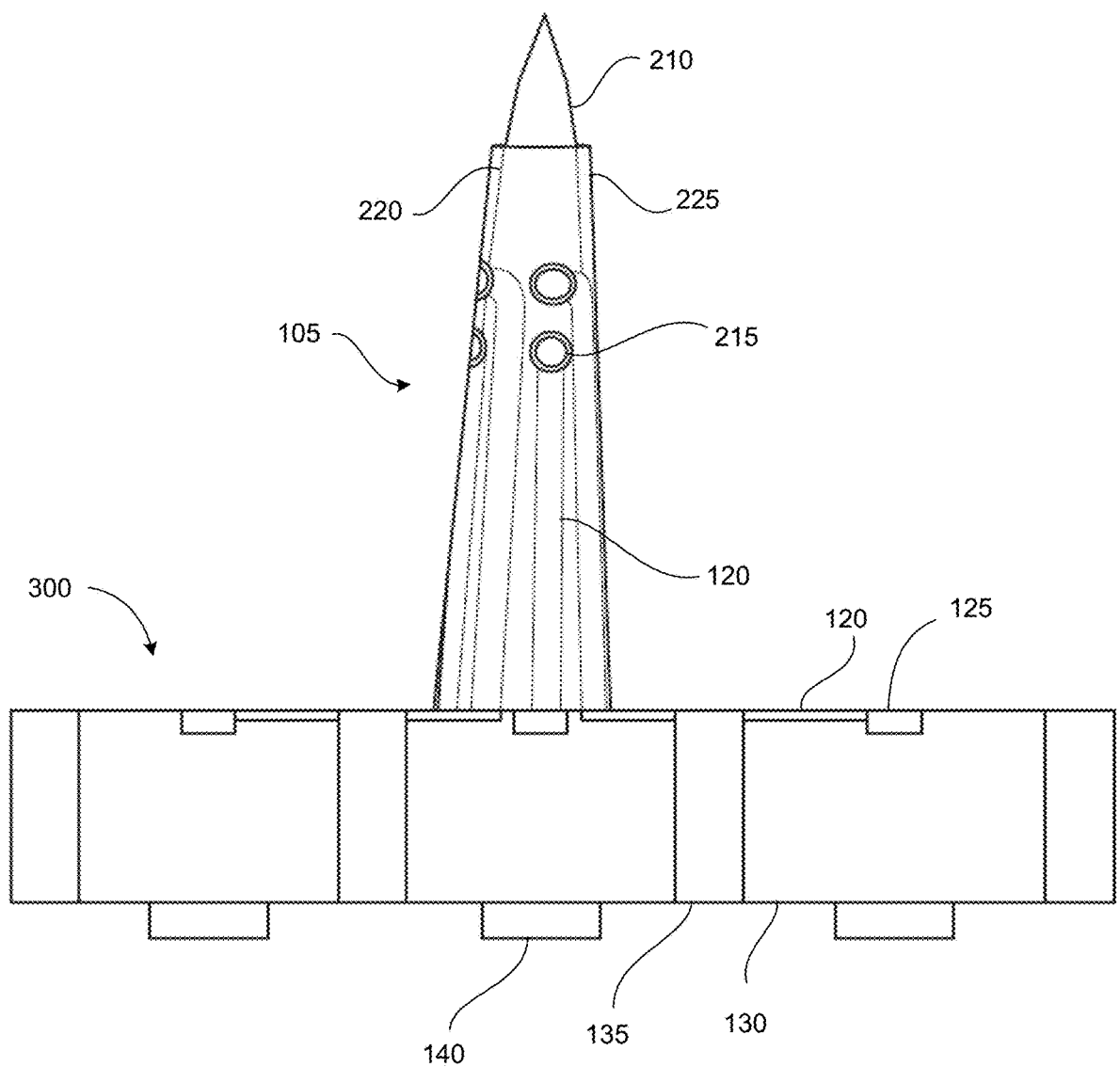
FIG. 4 is a side view of a microneedle attached to a 3×3 grid substrate in accordance with an embodiment of the present technology.

FIG. 4 shows a side view of the microneedle 105 of FIG. 2 attached to the 3×3 grid unit 300 of FIG. 3. As shown, the lead lines 120 run from the circular electrically active sites 215 on the shaft of the microneedle down to the surface of the substrate, and then across the surface to the base contacts 125. Electrical signals can travel from the electrically active sites, through the lead lines to the base contacts, and then through the silicon wells 130 to the bond pads 140.

It should be noted that the embodiment shown in these figures is but a single specific example of the present technology. Other embodiments can differ in structure, arrangement, materials, and so on.

As shown in FIG. 1, the multi-site electrode array can include a microneedle array including a plurality of microneedles supported on a base substrate. This microneedle array can be a two dimensional array, meaning that the microneedles are distributed in two dimensions across the substrate. In the embodiment shown in FIG. 1, the microneedle array is a 5×5 array in the shape of a square. Other sizes and shapes of arrays can also be used. For example, a 10×10 array or larger can be used. The array can be in the shape of a square, circle, elongated rectangle, or other shapes depending on the shape of the neuronal area in which the electrode array is to be implanted.

The size and spacing of the microneedles can generally be suitable for implanting the electrode array into cortical or nerve tissue, for measuring or stimulating neuronal activity without causing undue insult to the tissue. In one specific embodiment, the microneedles can have a circular diameter of about 80 micrometers. In other embodiments, the diameter of the microneedles can be from about 5 microns to about 100 microns. The microneedles can be substantially parallel to one another, and spaced apart so that the microneedles do not touch each other. The microneedle spacing can be about 20 micrometers to about 500 micrometers, center to center. In a specific embodiment, the microneedles can be spaced about 400 micrometers apart, center to center. The length of the microneedles can vary, but generally can be from about 100 micrometers to about 2000 micrometers, about 400 micrometers to about 1600 micrometers, or from about 800 micrometers to about 1200 micrometers.

In the previously developed Utah Electrode Array (UEA), a 10×10 array of microneedles was used with each microneedle having one electrically active site at its tip. The microneedles were spaced about 400 micrometers apart, and the entire array was about 4 mm by 4 mm in size. Using multiple electrically active sites per microneedle, in according with the present technology, this same array can be improved to have an increased total number of electrically active sites within an array of the same size. For example, if each microneedle includes an electrically active tip and eight additional electrically active sites on the shaft, then the total number of electrically active sites in the array can be increased nine-fold. In a specific embodiment, the multi-site electrode array can have 900 electrically active sites, resulting in 56.25 electrically active sites per mm$^2$.

In the embodiment shown in FIG. 1, the electrode array has a 5×5 array with 225 electrically active sites. Each microneedle is associated with a 3×3 grid of silicon wells separated by glass kerfs. In the embodiment shown, the pitch of the glass kerfs is about 133 micrometers. The silicon wells can be doped so that the wells are electrically conductive. The electrically conductive material in each well reaches through the entire depth of the base substrate, and is accessible from the back side of the substrate. The center well in each 3×3 grid maintains electrical contact with the electrically conductive core of the microneedle shaft. Because the core of each microneedle maintains electrical contact with its tip, the back side of the center well in each 3×3 grid is the point of contact for sending or receiving signals from the electrically active site at the corresponding microneedle tip. The base of each microneedle is small enough to fit within the 133×133 micrometer grid, and upon etching, is reduced to a circular diameter of about 80 micrometers. Lead lines formed of electrically conductive material deposited along the microneedle independently connect each one of up to 8 electrically active sites near the tip of the microneedle to one of the 8 wells in the surrounding base substrate. Because the electrically conductive wells reach through the entire depth of the base substrate, the back side of the substrate is an access point to which external wires or bumps can be bonded for connection to additional electronic components to individually address the electrically active sites on the shaft.

Although a 3×3 grid is exemplified, other grid sizes can be used. For example, the grid can be 4×4 with a 100 micrometer kerf pitch, 5×5 with an 80 micrometer kerf pitch, or other suitable grid size. The kerf pitches disclosed above are appropriate for use with a microneedle array having a microneedle spacing of 400 micrometers. If another microneedle spacing is used then the kerf pitch can be adjusted appropriately.

In some cases, the microneedles and the base substrate can be formed of a contiguous and common material. In one specific embodiment, the material can be doped silicon. Specifically, the microneedle cores and the silicon wells of the substrate can be formed from a common material. Other materials are also added to the electrode array, such as glass, insulating coatings, electrically conductive lead lines, and so on.

In some embodiments, transistor gates can be oriented on an underside of the base substrate. Each electrically active site can connect to a controller and a current source through a transistor gate.

Figure 5:
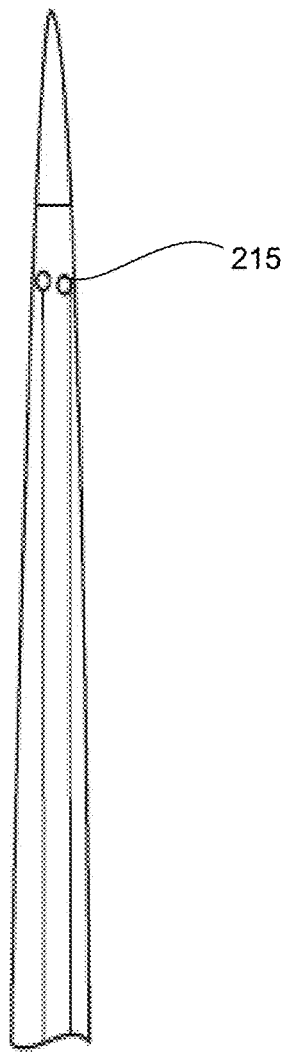
FIG. 5 is a close up view of a microneedle having a single tetrode arrangement of electrically active sites, in accordance with an embodiment of the present technology.

The electrically active sites across all the microneedles in the array can have a spatial configuration such that the electrically active sites form a three-dimensional volume of electrically active sites. The electrically active sites can be arranged in a variety of configurations. For example, the electrically active sites shown in FIG. 2 are circular electrically active sites. Additional embodiments are shown in FIGS. 5-8. FIG. 5 shows a microneedle with circular electrically active sites 215 arranged in a tetrode, or single-tetrahedral, pattern. The electrically active tip, two circular electrically active sites on the front side of the shaft, and one circular electrically active site on the back side of the shaft (not shown) form the four points of the tetrode. In this configuration, each single microneedle effectively acts as a tetrode. In one embodiment, the four recording sites can be arranged as vertices of tetrahedron, with one vertex at the tip of the shank and the remaining three vertices equally spaced on circumference of the shank and equidistant from the tip of the shank. This configuration can be used to triangulate neuronal sources. The described design readily allows for examining various arrangements of the tetrode configuration by adjusting the distance between the electrically active sites near the tip and the three shaft sites. It is possible to develop a multi-dimensional linear equation that relates the magnitude of the voltage observed at each electrically active site as a function of the location of each of the four sites' position relative to the neuronal source.

Figure 6:
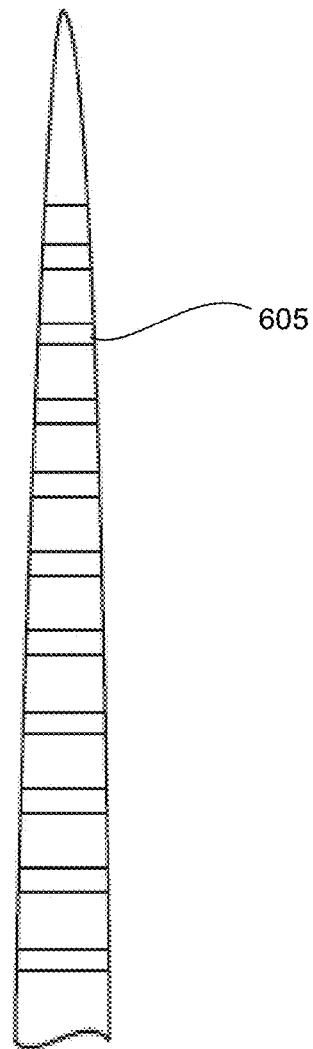
FIG. 6 is a close up view of a microneedle having electrically active ring sites in accordance with an embodiment of the present technology.

FIG. 6 shows a microneedle with electrically active sites 605 arranged as rings on the length of the shaft. Such a ringed microneedle can be used to perform laminar analysis. The ring sites can be used to simultaneously examine multiple lamina and perform temporal correlation studies. This configuration is easier to use for laminar analysis than conventional single shaft electrodes, which must be advanced or retracted to examine different cortical depths individually. Spacing between the ring sites can range from about 10 to about 500 micrometers. The ring sites can have widths ranging from about 10 to about 100 micrometers. Lead lines can connect the ring sites to base contacts on the substrate.

Figure 7:
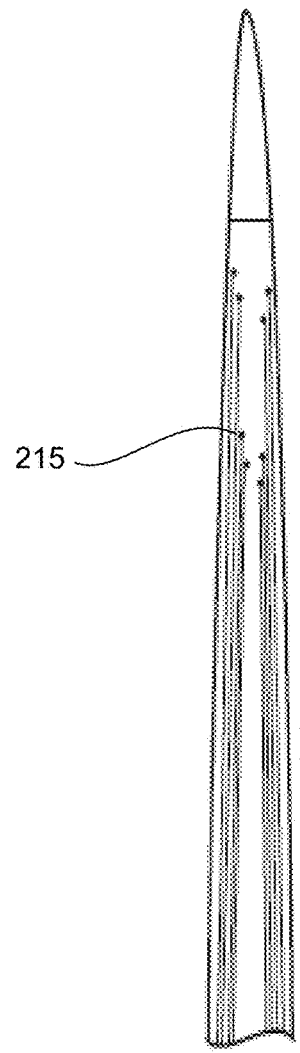
FIG. 7 is a close up view of a microneedle having multiple tetrode clusters of electrically active sites.

FIG. 7 shows a multiple-tetrahedral microneedle. In this configuration, electrically active sites 215 are placed in clusters of four at various points along the microneedle shaft. The clusters of four sites can act as tetrodes. Therefore, this arrangement can provide for both tetrode recording and laminar analysis. In the multiple-tetrahedral design, the active sites can be spaced apart by about 5 to about 100 micrometers. The distance between tetrode groups can range from about 10 to about 500 micrometers.

Figure 8:
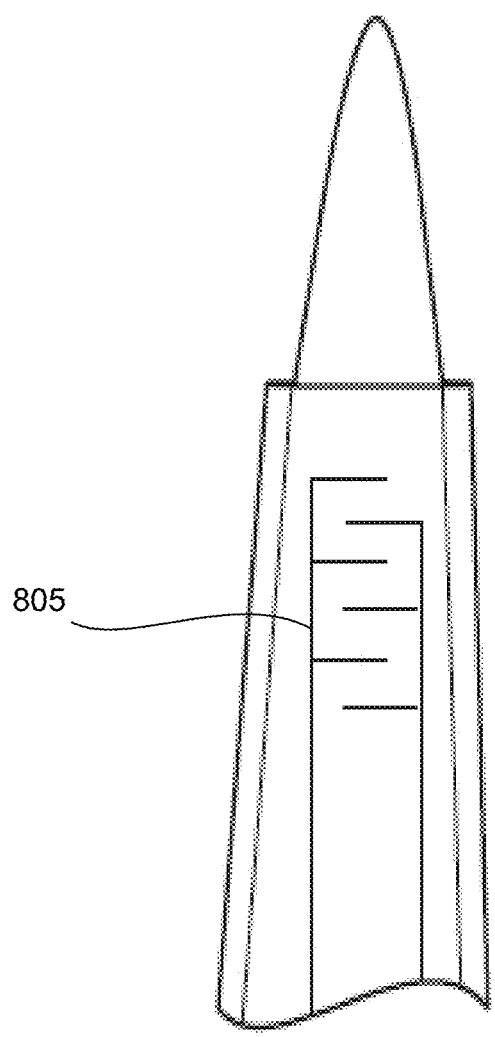
FIG. 8 is a close up view of a microneedle having an interdigitated electrode sensor in accordance with an embodiment of the present technology.

An additional configuration for the electrically active sites is shown in FIG. 8. This figure shows a microneedle having an interdigitated electrode active site 805. Such interdigitated electrodes can be used as device sensors to monitor device performance, pH sensors for tissue health, or oxygen sensors. Other materials can also be integrated to form sensors. Though recording of the unit activity of the brain is fundamental for the advancement of the neuroscience, the brain contains many other signal sources that are equally rich in information. For example, the level of oxygen in hemoglobin changes within 200 milliseconds after activity onset. In the literature, oxygen pressure changes have been shown to be highly specific for local increase in neural activity and the type of stimuli. Therefore, an integrated oxygen sensor can be formed on a shaft of a microneedle for measurement of oxygen level and electrical recording simultaneously. Furthermore, with the addition of in situ sensors such as oxygen and/or pH sensors greater understanding of foreign body response to the implanted device may be possible.

The active sites can be used for neural recording and stimulation. Fabrication of different patterns, such as active sites in tetrode and/or laminar configurations, enables triangulation of signals for locating subject neurons. Further, device and tissue health monitoring at the site of implantation can be achieved by the use of specific active site patterns, such as the interdigitated electrode shown in FIG. 8.

Figure 9:
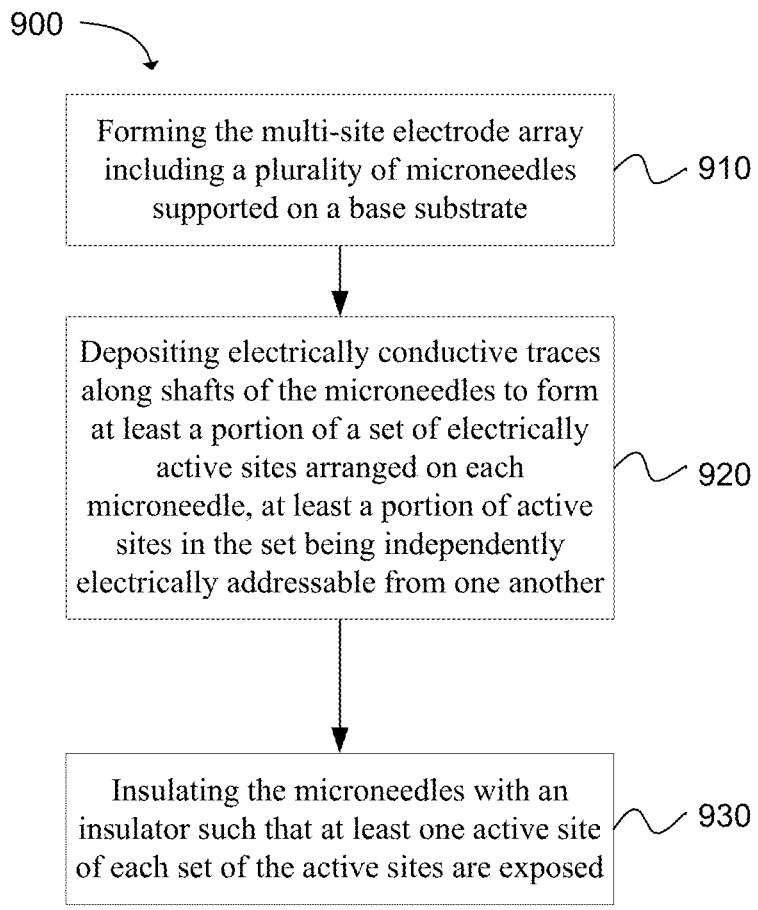
FIG. 9 is a flowchart illustrating a method of making a multi-site electrode array in accordance with an embodiment of the present technology.

The present technology also extends to methods of making multi-site electrode arrays. In one embodiment illustrated as a flow chart in FIG. 9, a method 900 of making a multi-site electrode array can include forming an array including a plurality of microneedles supported on a base substrate 910. After forming the microneedles, electrically conductive traces can be deposited along shafts of the microneedles to form at least a portion of a set of electrically active sites arranged on each microneedle 920. At least a portion of the active sites in the set can be independently addressable from one another. The microneedles can then be insulated with an insulator but at least one active site of each set of active sites can remain exposed 930.

Figure 10A:
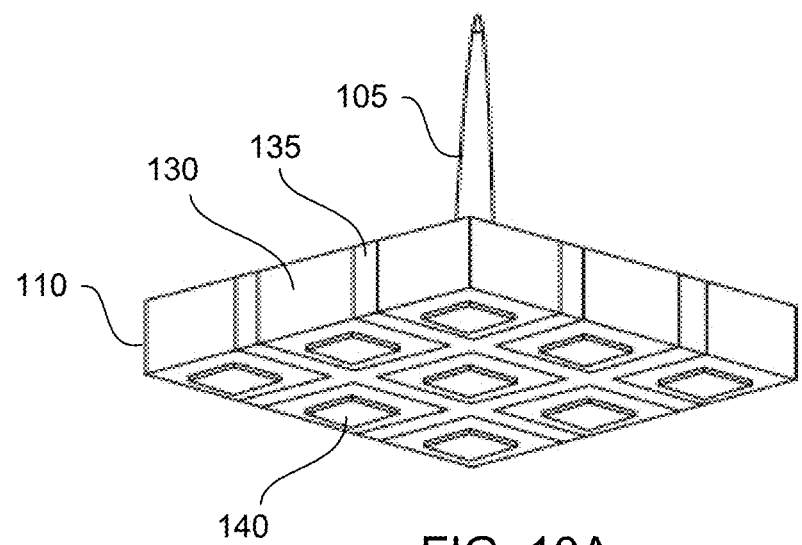
FIGS. 10A-10I show steps in a method of making a multi-site electrode array in accordance with an embodiment of the present technology.
Figure 10B:
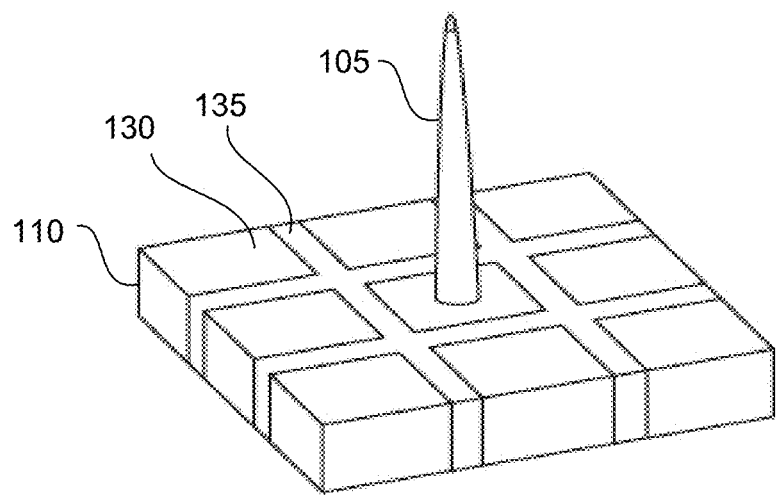
Figure 10C:
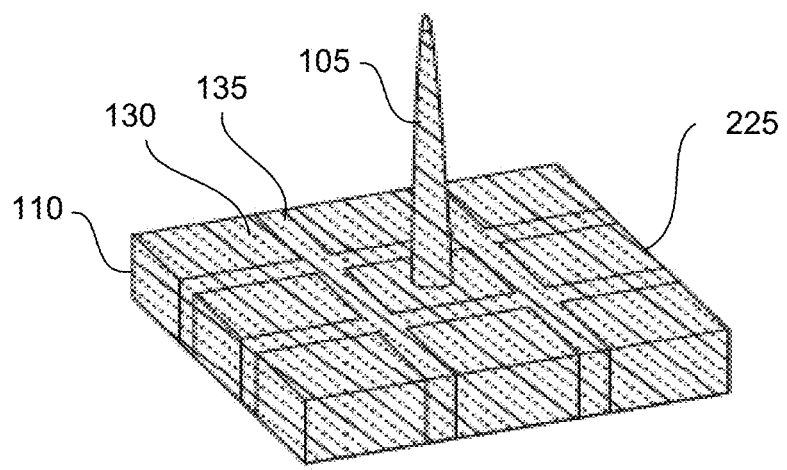
Figure 10D:
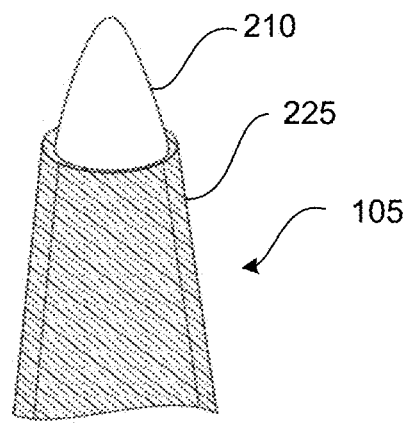

Steps of a specific method of making a multi-site electrode array are shown in FIGS. 10A-10I. These figures show only a single microneedle with a corresponding 3×3 grid of the substrate. However, the methods can be extended to form an array with any number of microneedles. FIGS. 10A and 10B show a microneedle 105 on a 3×3 grid of a substrate 110. The substrate includes silicon wells 130 separated by glass kerfs 135 and bond pads 140 on the bottom of each silicon well. The method begins by forming an array of microneedles as shown in FIGS. 10A and 10B. Then, as shown in FIG. 10C, an insulating coating is applied to the microneedle and substrate. FIG. 10D shows a close up of an exposed tip 210 of the microneedle. The tip can either be re-exposed after applying the insulating coating to the entire microneedle, or the insulating coating can be applied such that the tip is never covered with the insulating coating. One particular method of applying an insulating coating while leaving the tip exposed is described in U.S. patent application Ser. No. 11/807,763, entitled "MASKING HIGH ASPECT-RATIO STRUCTURES," which is incorporated herein by reference.

Figure 10E:
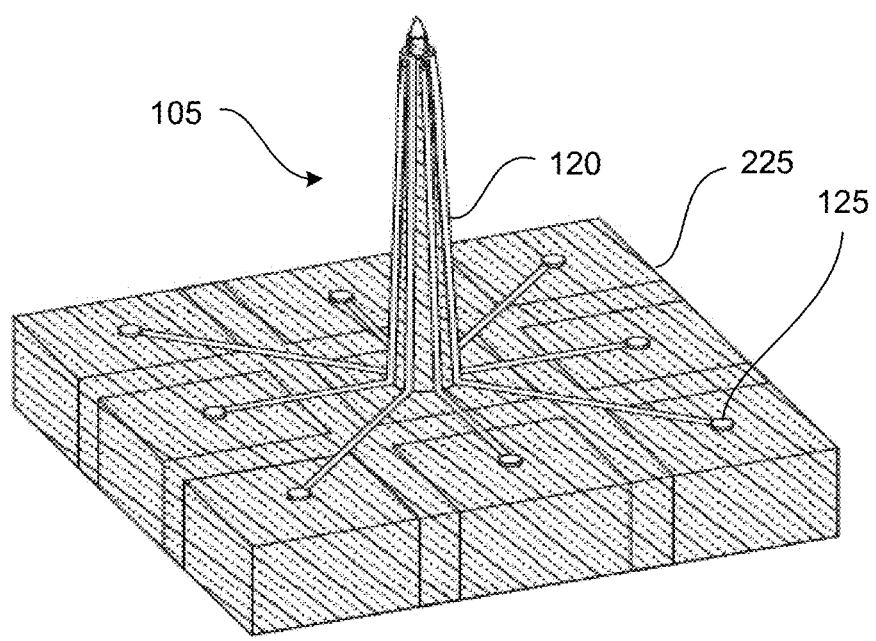
Figure 10F:
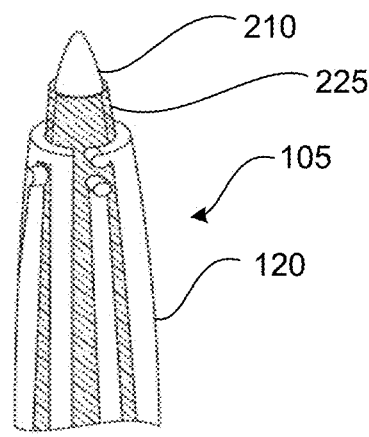

The next step in the method is shown in FIG. 10E. Electrically conductive traces 120 are deposited on top of the insulating layer 225. The traces run from near the tip of the microneedle, down to the base of the microneedle, and then branch out across the surface of the substrate to base contacts 125. In the embodiment shown, eight traces lead to eight base contacts on the eight silicon wells surround the central silicon well that is connected to the tip of the microneedle. The base contacts are formed to be electrically connected to the silicon wells, e.g., the base contacts penetrate through the insulating layer to make contact with the silicon wells. FIG. 10F shows a close up of the microneedle with the exposed tip 210 and the traces formed on top of the insulating layer. Because the traces do not touch each other, and because an insulating layer is between the traces and the conductive tip of the microneedle, all of the traces and the tip are electrically isolated one from another.

Figure 10G:
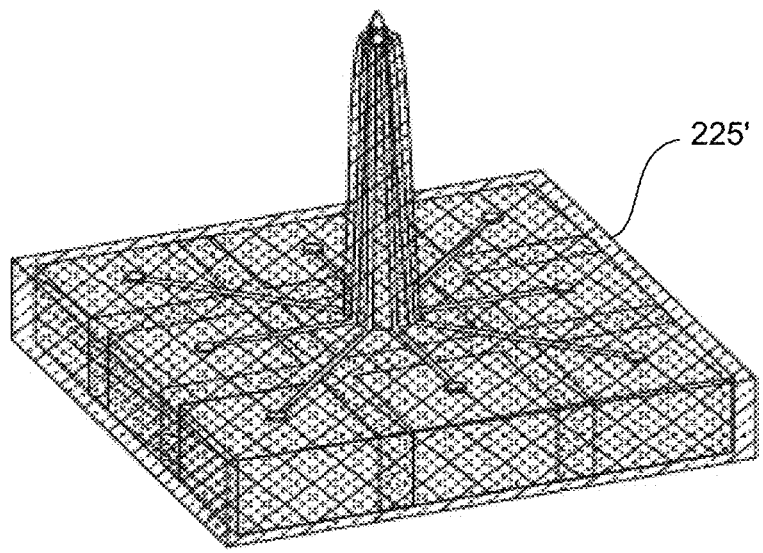
Figure 10H:
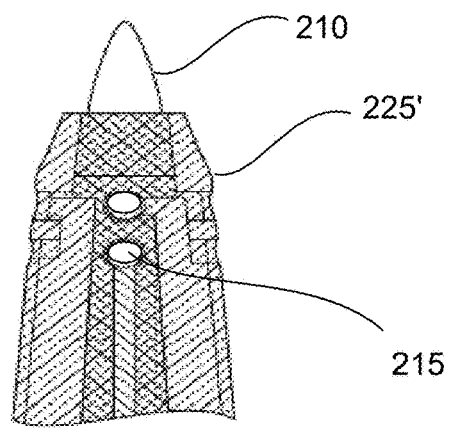
Figure 10I:
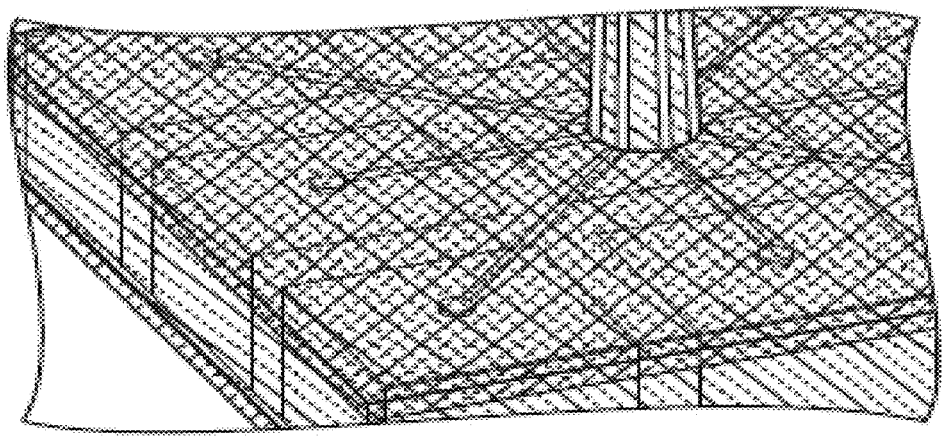
Figure 11:
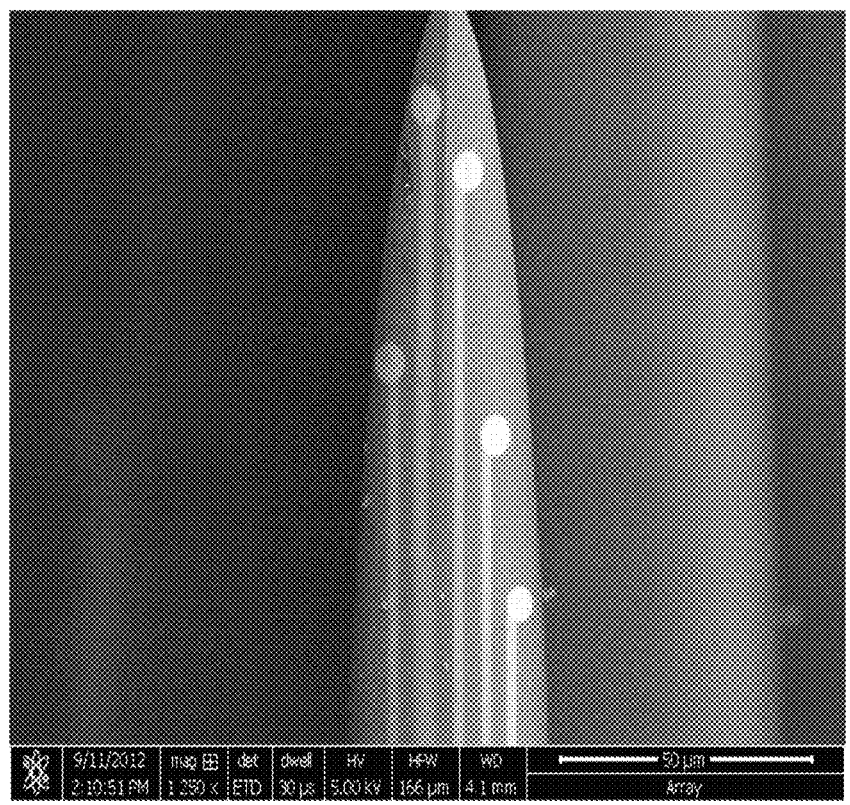
FIG. 11 is a SEM micrograph of a microneedle having circular electrically active sites in accordance with an embodiment of the present technology.
Figure 12:
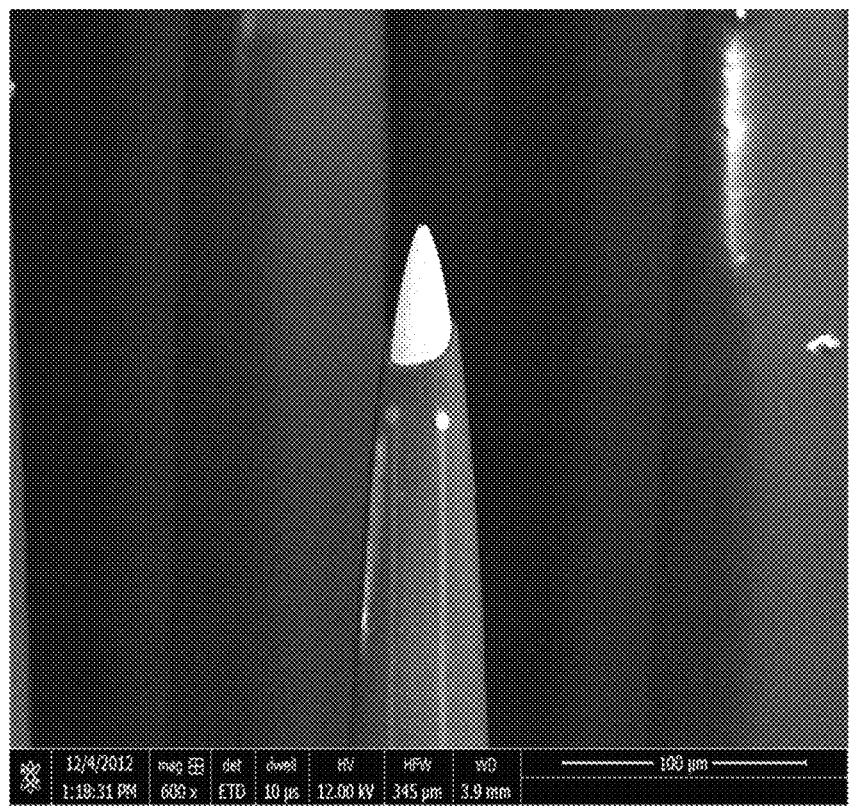
FIG. 12 is a SEM micrograph of a microneedle having circular electrically active sites in accordance with an embodiment of the present technology.
Figure 13A:
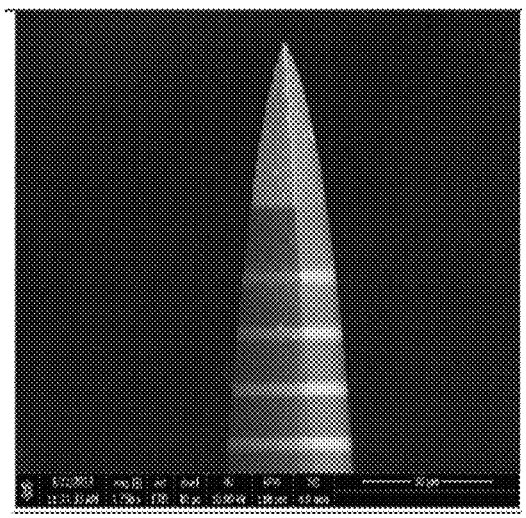
FIGS. 13A and 13B are SEM micrographs of a microneedle having ring electrically active sites in accordance with an embodiment of the present technology.
Figure 13B:
Figure 14A:
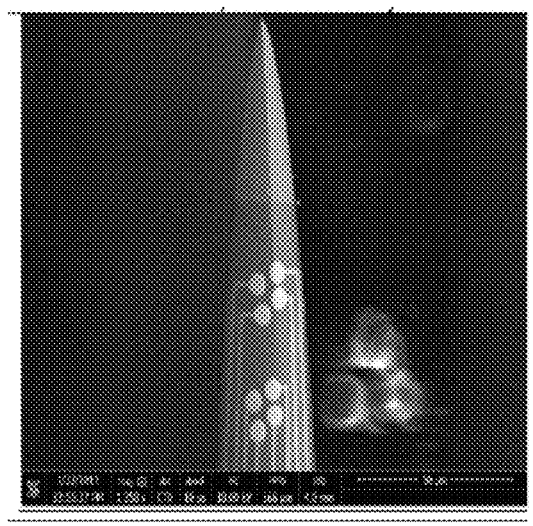
FIGS. 14A and 14B are SEM micrographs of a microneedle having multiple tetrode electrically active sites in accordance with an embodiment of the present technology.
Figure 14B:
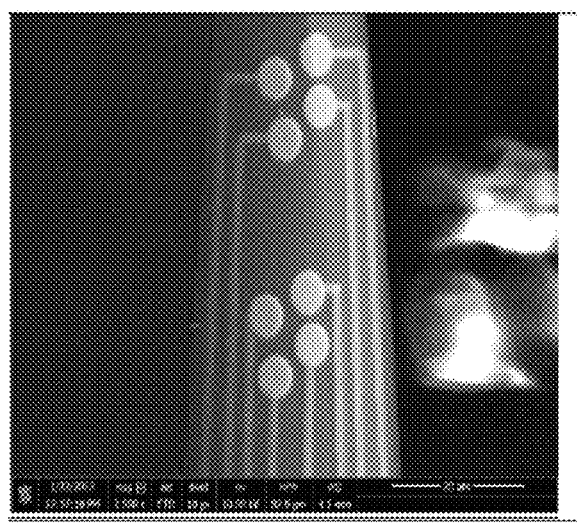

Next, as shown in FIG. 10G, a second insulating coating 225' can be applied to the microneedle and substrate. This insulating coating layer covers the traces and base contacts that were deposited in the previous step. However, as shown in FIG. 10H, the tip 210 of the microneedle remains exposed. Additionally, the electrically active sites 215 remain exposed. The electrically active sites can be covered by the second insulating coating and then re-exposed, or the second insulating coating can be applied in such a way that the electrically active sites are not covered. FIG. 10I shows a close up of the substrate with the two insulating coatings applied. The traces leading from the electrically active sites to the bas contacts are above the first insulating layer, but below the second insulating layer. Thus, the only portions of the traces that are exposed to the neural environment are the electrically active sites.

When forming the traces and electrically active sites, the electrically active sites can be formed in any of the configurations described herein. Thus, in some embodiments, the step of depositing the traces can include forming a tetrode of electrically active sites on each microneedle. The tetrode can include the tip site and three additional side shaft sites, and in some cases all four active sites can be oriented along the shaft. In other embodiments, the side shaft sites can be deposited at shaft surface locations equidistant from the tip site, such that the tetrode of four electrically active sites forms a tetrahedron. In yet other embodiments, a set of electrically active sites can include a tip site and a plurality of ring sites. The ring sites can circumscribe the microneedle shaft near the tip. The rings sites can be oriented at progressively greater distances from the tip. In still other embodiments, the electrically active sites can be in multiple clusters along the shaft of the microneedle.

Any suitable method can be used for forming the electrically conductive traces. One particularly useful method is focused ion beam (FIB) deposition. A focused ion beam (FIB) tool, equipped with a high resolution scanning electron microscope (SEM), can be used to form metal trace patterning along the shafts of the microneedles. This technology allows one to literally write with metal. Exemplary metals that can be used in FIB include platinum, iridium, gold, and others. In a specific embodiment, platinum can be used to form the traces. FIB deposition can be used to pattern metal on the shafts of the microneedles with precise control and reproducible resolution of less than one micrometer. Metal can be patterned in various configurations of any shape, size, number and location on the tip or along the shaft of the microneedles. A clear advantage in using FIB to define the pattern of electrically active sites and traces is the capability of repeatedly and reproducibly achieving nanometer-scale critical dimensions. FIB uses a collimated ion beam of nanometer scale. The stage on which the substrate is secured can be tilted, rotated, and moved in any direction to access the entire surface area of each microneedle as well as the 3×3 grid substrate base beneath each microneedle. A line of sight to an area allows depositing or etching that area using the ion beam.

FIB can also be used to ablate materials. For example, FIB can be used to remove the insulating coating from the microneedle tip and the electrically active sites on the microneedle shaft. In some examples, the insulating coating can contain parylene-C, alumina, silicon nitride, combinations thereof, bilayers thereof, or the like. FIB can be used to ablate these materials to expose the electrically active sites. In one particular example, the insulating coating can contain parylene-C.

This FIB can also be equipped with high-resolution scanning electron microscopy (SEM). The combination provides unique capabilities of fast and precise metal contact patterning. A combination of large electric fields and electrostatic lenses cause ionization of a gallium ion source, accelerates, and focuses the gallium ions into a high density ion beam. This ion beam can be scanned similarly to the electron beam of a SEM, and as such can be used to etch or deposit in controllable patterns at the nanometer scale. Ablation, or etching, occurs due to the high momentum ions bombarding the sample and introducing damage analogous to sand blasting. Deposition can also be done giving the right conditions and presence of a precursor. The precursor often is an organometallic gas. In one case, trimethylcyclopentadienyl-platinum [$(CH_3)_3CH_3C_5H_4Pt$] is used. This gas is introduced to the area through a needle which is positioned close the desired location. The conditions of the ion beam are then adjusted such that the energy is sufficient to decompose the organometallic bond. The platinum is then deposited on the sample in the pattern the beam scan defines. The ion beam can reach the shaft of an inner microneedle of the array as long as the microneedle can be imaged with line of sight. This allows patterning of any area which can be imaged even if the geometries do not produce the optimum efficiency. With the ability to tilt and rotate the stage, even inner shafts can be patterned.

The precision, consistency, and reproducibility of the electrically active sites formed using FIB can provide predictable electrical and spatial characteristics. This can allow the sites to be grouped in a manner that enables precise, predictable, and selective tuning of neural interface regions. The ability of FIB technology to "write" on the shafts of the three-dimensional microneedle structure allows fabrication of in-situ sensors on the shaft of the UEA, as shown in FIG. 8. The FIB and multisite technology can be implemented to form any configuration of electrode array. For example, the electrode array can be a two dimensional array of microneedles in which microneedles have substantially the same height. In other examples, the electrode array can be a slanted electrode array such as the Utah Slant Electrode Array (USEA), a convoluted electrode array, or high aspect ratio geometries. For example, if the presented multisite technology is implemented in the USEA it would lead to a high electrode density (56.25 electrodes/mm$^2$) interface that can provide greater access to nerve fibers. By keeping a small set of single elements, complex electrode site configurations can be fabricated. Depending on the use requirements, the number of sites and/or the site spacing can be varied without any change in the assembly methods of the device.

In another example, depositing the electrically conductive traces can be accomplished by electrochemical deposition. This can be performed after the first insulating coating has been applied. After the traces have been deposited, a second insulating coating can be applied and then FIB can be used to expose the electrically active sites. Alternatively, electrically conductive traces can be deposited by sputtering or evaporation techniques using a shadow mask. Although any number of materials can be used, non-limiting examples of suitable shadow mask material can include silicon nitride, silicon dioxide, polymers, and the like. In one example, a pattern can be formed in the shadow mask via etching, laser ablating, or the like. Regardless of the specific deposition technique, non-limiting examples of conductive materials can include Pt, Au, Ir, IrO$_x$, TiN, conductive polymers such as PEDOT, and the like.

In another embodiment, the method can include surface treating at least portions of the array to form pseudoporous surfaces.

Although the above discussion has focused on multi-site electrode arrays, the methods described above can also be used to form multi-site channel arrays. A multi-site channel array can include a plurality of microneedles supported on a base substrate. A set of channels can be arranged on each microneedle. Each channel can be independent of the others. Each channel can have an active sit at a distal end of the channel. In some cases, a portion of the set of channels can be conduits adapted for communication of light to the active site. In other cases, a portion of the set of channels can be conduits adapted for communication of a fluid to the active site. The fluid can be a pharmaceutically active agent. For example, one or more fluid conduits can be formed from a fluid reservoir to the active site. The fluid reservoir can be sized to retain a volume of fluid sufficient for a desired physiological result. In some examples, the fluid can include or consist of the pharmaceutically active agent. Alternatively, the fluid can include a release modifier, crosslinked polymer matrix, hydrogel, or other agent adapted to control rate of release of the pharmaceutically active agent from the fluid reservoir.

Based on the above principles, the FIB deposition approach can be slightly modified to form a set of channels instead of depositing traces. Specifically, FIB can be performed without a metal source (e.g. platinum) resulting in etching of a target. Accordingly, a multi-site channel array can include a microneedle array having a plurality of microneedles supported on a base substrate. A set of channels can be arranged on each microneedle, each channel in the set being independent of one another and having an active site at a distal end of the channel. These channels can be formed via FIB as recessed channels along the shafts. The channels can optionally be enclosed, except at ends thereof through any suitable technique. For example, a sacrificial material can be embedded in the channels, followed by deposition of an outer channel layer. Subsequently, the sacrificial material can be removed to leave an open channel. Similarly, an outer layer can be wrapped or formed around the shaft which leaves the channels open to fluid passage. Alternatively, a waveguide material can be embedded in the etched channel (e.g. optical fiber or other suitable waveguide material). Thus, at least a portion of the set of channels can be conduits adapted for communication of light to the active site. Such an approach can allow for delivery of light to tissue for various therapeutic treatments. Alternatively, or in addition, at least a portion of the set of channels can be conduits adapted for communication of a fluid to the active site. In these embodiments, the conduits can be used for delivery of drugs or other pharmaceutically active agents.

Generally, the multi-site electrode arrays disclosed herein open new possibilities for neuroscience researchers. The multi-site electrode arrays improve upon previous solutions such as the UEA for understanding neuronal activity by providing recordings sites in a three dimensional region of cortex. The multi-site electrode array presents a short path towards product validation and clinical implementation, as the innovation utilizes a majority of the same structure and materials as the UEA, an FDA approved and clinically viable precedent device. As compared to the conventional UEA, the multi-site electrode array design adds three steps to the device fabrication process. The higher density of electrically active sites in the multi-site electrode array as compared to the UEA is achieved without increasing the footprint of the device, resulting in comparable tissue damage. The multi-site electrode array provides a multi-channel neuromodulation electrode array with an easily customizable electrode site arrangement. For stimulation and recording, this will enable the full freedom for field steering and three-dimensional spatial mapping of neural activity source.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

EXAMPLES

In the Nanofab facility at the University of Utah in Salt Lake City, Utah, there is a FIB tool (FEI Helios Nanolab 650i dual beam FIB) capable of platinum and iridium deposition. FIGS. 11-14 show SEM micrographs of microneedles patterned by the FIB tool. The nominal Pt thickness was ~1 micrometer, and the width range was from 2 to 30 micrometers. The ion beam deposition conditions were carefully chosen to avoid significant damage of the sample if the etch rate exceeds the deposition rate. With the parameters used to deposit platinum on the electrode shaft, no evidence of such damage by SEM was found.

Once the platinum was patterned the device was encapsulated with a second insulating coating. The coating included parylene-C. The active sites were de-insulated by ablating parylene-C using FIB. Caution was taken to make sure underlying platinum was not damaged. This was done by monitoring the electron signal for an increase in brightness once the platinum was exposed. Furthermore, adhesion testing was done to examine parylene-C and platinum adhesion. Adhesion testing of the platinum and parylene-C on the underlying substrate was examined by ten high velocity insertions into 2% agarose. This is the procedure that was previously used for testing the UEA. The materials were inspected for any damage, delamination or anomaly in the materials by optical inspection and under SEM. No delamination was detected under SEM or by visual inspection.

What is claimed is:
1. A multi-site electrode array comprising:
 a) a microneedle array including a plurality of rounded microneedles supported on a base substrate; and
 b) a set of electrically active sites arranged on each microneedle, wherein each microneedle includes:
  an electrically conductive core;
  an electrically active site on a front side of a shaft of the microneedle and another electrically active site on a back side of the shaft of the microneedle,
  wherein at least one active site on the front side and at least one active site on the back side are not ring sites, and
  an independent lead line deposited along a shaft portion of the microneedle for each electrically active site,
  wherein a layer of insulating coating is oriented between the independent lead line and the electrically conductive core to isolate each active site in the set such that each active site is independently electrically addressable.
2. The array of claim 1, wherein the array is a two dimensional array such that the plurality of microneedles are distributed in two dimensions across the base substrate.
3. The array of claim 1, wherein the plurality of microneedles are substantially parallel to one another.
4. The array of claim 1, wherein the microneedles and the base substrate are formed of a contiguous and common material.
5. The array of claim 1, wherein a spatial configuration across the plurality of microneedles for the sets of electrically active sites forms a three-dimensional volume of electrically active sites.
6. The array of claim 1, wherein at least a portion of the electrically active sites are electrically connected to a base contact via independent lead lines formed of an electrically conductive material deposited along the shaft portion of the microneedles for each electrically active site, wherein at least a portion of the base contacts are electrically independent of one another.
7. The array of claim 1, further comprising transistor gates and pads oriented on an underside of the base substrate and adapted to independently connect each electrically active site to a controller and a current source.
8. The array of claim 1, wherein the set of electrically active sites includes a tip site of the electrically conductive core and a plurality of side shaft sites such that the tip site and the plurality of side shaft sites are electrically isolated by the layer of the insulating coating.

9. The array of claim 8, wherein the side shaft sites are selected from the group consisting of ring sites, spot sites, interdigitated electrodes, and combinations thereof.

10. The array of claim 8, wherein the side shaft sites are interdigitated electrodes such that the array is a sensor.

11. The array of claim 8, wherein at least a portion of the plurality of side shaft sites are oriented at varying distances from the tip site.

12. The array of claim 1, further comprising the electrically insulating coating between the plurality of independent lead lines and the electrically conductive core over the microneedle array such that at least one active site from the set of electrically active sites is exposed.

13. The array of claim 1, wherein the array is a two dimensional array such that the plurality of microneedles are distributed in two dimensions across the base substrate, and wherein the microneedles and the base substrate are formed of a contiguous and common material.

14. The array of claim 1, wherein the electrically active sites include ring sites, or a tetrode arrangement including a tip site of the electrically conductive core and three side shaft sites such that the tip site and the plurality of side shaft sites are electrically isolated by the layer of the insulating coating.

15. The array of claim 1, wherein the microneedles have a circular cross-section.

16. A method of making a multi-site electrode array, comprising:
   a) forming the multi-site electrode array including a plurality of rounded microneedles supported on a base substrate, wherein each microneedle includes an electrically conductive core;
   b) depositing electrically conductive traces along shafts of the microneedles to form at least a portion of a set of electrically active sites arranged on each microneedle with an electrically active site on a front side of the shaft and another electrically active site on a back side of the shaft and wherein at least one active site on the front side and at least one active site on the back side are not ring sites, at least a portion of active sites in the set being independently electrically addressable from one another via an independent lead line for each electrically active site; and
   c) insulating the microneedles with an insulator such that at least one active site of each set of the active sites are exposed and the insulator is oriented between the electrically conductive traces and the electrically conductive core to isolate each active site in the set such that each active site is independently electrically addressable.

17. The method of claim 16, wherein the depositing further includes forming a tetrode of electrically interactive sites on each microneedle, the tetrode including a tip site and three additional side shaft sites.

18. The method of claim 17, wherein the side shaft sites are deposited at shaft surface locations equidistant from the tip site such that the tetrode of four electrically active sites form a tetrahedron.

19. The method of claim 16, wherein the set of electrically active sites includes a tip site and a plurality of ring sites, said ring sites circumscribing the microneedle shaft near the tip site, and wherein the ring sites are oriented at progressively greater distances from the tip site.

20. The method of claim 16, wherein the portion of the set of active sites form multiple clusters along the shaft of the microneedle.

21. The method of claim 16, wherein the depositing is accomplished via focused ion beam (FIB) deposition.

22. The method of claim 16, wherein the insulator includes parylene-C, and exposure of active sites is accomplished by ablating parylene-C via focused ion beam deposition (FIB).

23. The method of claim 16, wherein the depositing electrically conductive traces is performed by electrochemical deposition after the insulating, wherein portions of the insulator has been selectively removed via focused ion beam deposition (FIB) ablation in a pattern to expose areas defining the electrically interactive sites and traces.

24. The method of claim 16, wherein the depositing electrically conductive traces is performed by sputtering or evaporation using a shadow mask.

25. The method of claim 16, further comprising surface treating at least portions of the array to form pseudoporous surfaces.

* * * * *